United States Patent [19]

Orth et al.

[11] Patent Number: 4,549,024

[45] Date of Patent: Oct. 22, 1985

[54] OXIDATION OF QUINOLINE TO QUINOLINIC ACID

[75] Inventors: Winfried Orth, Hassloch/Pflaz; Emmerich Pastorek, Hemsbach; Werner Fickert, Mannheim, all of Fed. Rep. of Germany

[73] Assignee: Rutgerswerke Aktiengesellschaft, Fed. Rep. of Germany

[21] Appl. No.: 668,219

[22] Filed: Nov. 5, 1984

[30] Foreign Application Priority Data

Dec. 14, 1983 [DE] Fed. Rep. of Germany ....... 3345223

[51] Int. Cl.⁴ .......................................... C07D 213/807
[52] U.S. Cl. ................................................... 546/320
[58] Field of Search ......................................... 546/320

[56] References Cited

U.S. PATENT DOCUMENTS 2,586,555  2/1959  Mueller ............................... 546/320

FOREIGN PATENT DOCUMENTS 24197    2/1981  European Pat. Off. ............. 546/320
3150005  6/1983  Fed. Rep. of Germany ...... 546/320

Primary Examiner—Henry R. Jiles
Assistant Examiner—Dale A. Bjorkman
Attorney, Agent, or Firm—Bierman, Peroff & Muserlian

[57] ABSTRACT

A novel process for the preparation of quinolinic acid comprising reacting quinoline in an aqueous acid with hydrogen peroxide in the presence of at least one cation selected from the group consisting of vanadyl V, cobalt III, titanyl IV and osmium VIII cations at 50° to 100° C. and then oxidizing with chlorite or chlorate ions to form quinolinic acid.

6 Claims, No Drawings

OXIDATION OF QUINOLINE TO QUINOLINIC ACID

STATE OF THE ART

Quinolinic acid or pyridine-2,3-dicarboxylic acid is used in the manufacture of pharmaceutically effective compounds such as local anesthetics, bactericides and compounds that can be used against metabolic disorders. From the literature, various methods are known for producing quinolinic acid and they are based in part on the oxidation of quinoline and in part on the oxidation of activated quinoline derivatives substituted at the aromatic nucleus.

The method first described by Hoogewerff et al [Berichte der deutschen chemischen Gesellschaft Vol. 12, 747, (1879)- Reports of the German Chemical Society] oxidizing quinoline with potassium permanganate in an alkaline medium provides only very small yields of quinolinic acid as well as a large quantity of other undesired reaction products.

Other processes for the oxidation of quinoline are based essentially on oxidation with hydrogen peroxide in the presence of a copper salt as described by Stix et al [Chem. Bert. Vol. 65, 11 (1932)]. Since this reaction is rather difficult to manage, modifications were subsequently developed to obtain a better control of the reaction and a slight increase in the yield. Such changes have been disclosed in EP - A No. 0 024 197 or EP - A No. 0 034 943 but in all these processes, copper salts of quinolinic acid are created first, from which the free acid must be released wit the aid of a sulfide. This is an additional, undesired reaction step, but more importantly, it has became apparent that the complete separation of the copper ions is extremely difficult so that the quinolinic acids produced by these methods always contain traces of copper.

DE No. 31 50 005 A1 describes a simple, environment-friendly process for producing quinolinic acid of high purity and with good yields wherein quinoline derivatives are oxidized with chlorate ions with vanadyl (V)-cations serving as catalysts. The disadvantage of this process is that only such quinoline derivatives in which at least one hydrogen atom on the benzene nucleus is substituted by an activating group are oxidized into quinolinic acid while the easily accessible and cheap unsubstituted quinoline cannot be oxidized in this process.

OBJECTS OF THE INVENTION

It is an object of the invention to provide an economical, simple, pollution-free process for oxidizing quinoline to high purity quinolinic acid.

This and other objects and advantaqes of the invention will become obvious from the following detailed description.

THE INVENTION

The novel process of the invention for the preparation of quinolinic acid comprises reacting quinoline in an aqueous acid with hydrogen peroxide in the presence of at least one cation selected from the qroup consistinq of vanadyl V, cobalt II, titanyl IV and osmium VIII cations at 50° to 100° C. and then oxidizing with chlorite or chlorate ions to form quinolinic acid.

It has been found that in an acid, aqueous medium in the presence of catalytic quantities of cobalt (III), titanyl (IV), vanadyl (V) or osmium (VIII)-cations, quinoline reacts with hydrogen peroxide to form water-soluble oxidation products which oxidation reaction is not uniform and cannot be exactly reproduced. Accordingly, no defined oxidation products are created, either. If the oxidation is carried through until no more hydrogen peroxide reacts, a reaction in which substantially more hydrogen peroxide is required than the theoretical stoichiometric quantity for the formation of dicarboxylic acid, then an unprocessable mix of terminal hydroxyl and carboxyl fragments from the aromatic and the pyridine rings of the quinoline is obtained.

However, in the present process, this reaction is controlled in the sense of a preferred formation of quinolinic acid when the hydrogen peroxide is used to preoxidize quinoline and the oxidation into quinolinic acid with chlorite or chlorate ions is effected thereafter. It is assumed that in the preoxidation reaction step, an activation and/or splitting of the aromatic ring takes place, and in the second oxidation stage a targeted oxidation of the activated products into quinolinic acid takes place.

The quantity of hydrogen peroxide to be used in the invention must be less than the quantity of hydrogen peroxide consumed in a complete reaction with quinoline and is advantageously less than the quantity stoichiometrically needed for the production of pyridine dicarboxylic acid, and amounts to 20 to 90%, preferably 30 to 80% of this amount. With 20% of the amount of hydrogen peroxide stoichiometrically required, a yield of 44% quinolinic acid relative to the quinoline used is obtained after the chlorite or chlorate oxidation and the quinoline that was not converted can be recovered. With an increasing amount of hydrogen peroxide in the preoxidation step, the yield of quinolinic acid rises until it reaches a maximum with 51 to 52%, relative to the quinoline used, at 80% of the stoichiometrically required quantity of hydrogen peroxide.

However, at the same time, the quantity of the undesired, undefined oxidation products formed which can no longer be converted into quinolinic acid also increases so that when 90% of the stoichiometrically required amount is used, there is a sharp decrease in the yield of quinolinic acid.

The hydrogen peroxide used can be pure hydrogen peroxide in the form of its aqueous solutions, as well as its additive compounds such as alkali metal carbonate, alkali metal borate, phosphate or urea-peroxyhydrate.

The second oxidizing agent with which the preoxidized, activated products are oxidized into quinolinic acid are oxygen compounds of chlorine. As source for these, all water-soluble chlorites or chlorates can be used. Preferably, however, the chlorates of alkaline earth metals and alkali metals and of ammonium are used. Particularly suitable is the easily handable, anhydrous, but water-soluble sodium chlorate.

The quantity of chlorite or chlorate to be used is inversely proportional to the quantity of hydrogen peroxide used. To obtain a good yield and a fast ending of the oxidation reaction, it is appropriate to work with an excess of oxidizing agent equal to the sum of hydrogen peroxide and chlorite or chlorate. It was found that with 120 to 150%, preferably 130%, of the amount of oxidizing agent theoretically required for the oxidative production of quinolinic acid from quinoline, the greatest economy of the process of the invention is to be found.

Vanadyl (V) as well as cobalt (III) titanyl (IV) or osmium (VIII)-cations are used as catalyst for both oxidation reactions and they can be prepared by dissolving appropriate water-soluble salts in the acid reaction mixture. The amount of catalyst used for each reaction is between 0.01 and 0.1 g salt per mol of quinoline with a larger quantity of catalyst naturally leading to a higher reaction speed.

The reaction is effected in an acid, aqueous medium at temperatures in the range of 50° to 100° C. and particularly suited for use as acids are mineral acids such as hydrochloric acid, nitric acid, phosphoric acid or preferably sulfuric acid. Working up of the reaction mixture is effected by known methods.

In the following example there are described several preferred embodiments to illustrate the invention. However, it should be understood that the invention is not intended to be limited to the specific embodiments.

EXAMPLE 516 g (4 mol) of quinoline and 0.2 g of ammonium vanadate were dissolved in a mixture of 1.6 liters of water and 0.45 liters of concentrated sulfuric acid. The solution was heated to 65°–70°, and at this temperature it was stirred and 406 ml (10.8 mol) of 70% hydrogen peroxide was added during 3 to 4 hours. The reaction is slightly exothermic and to maintain the reaction temperature at 70° C. during the time hydrogen perioxide was added, it was sufficient to hold the water bath in which the reaction took place at approximately 60° C. After the oxidizing agent was added, the mixture was stirred for approximately 3 hours at 70°–75° C. and after this time, the hydrogen peroxide was consumed (checked with starch iodide paper!). The reaction mixture was heated to 85°–90° C. and a solution of 1384 g (15 mol) of sodium chlorate and 2 liters of water was added with stirring at 90°–100° C. over 3 hours. The reaction with sodium chlorate was highly exothermic at the beginning and the reaction mixture had therefore to be cooled. The initially light reaction solution became darker during the oxidation with hydrogen peroxide, and it turned still darker with sodium chlorate addition. Only at the end of the oxidation did the oxidation mixture turn light yellow.

During the oxidation with hydrogen peroxide, carbon-dioxide evolved from the reaction solution. The generation of gas increased when sodium chlorate was added in the second stage. Since explosive chlorine dioxide could form at the end of the oxidation, the waste gases were collected in an absorption vessel in which 50 g of sodium hydrosulfite were dissolved in 0.5 liters of water and 10 g of magnesium oxide.

After the oxidizing agent was added, the mixture was stirred for 3 hours at 90° C. At the end of the chlorate addition and during the after-reaction time, the equipment must be rinsed with carbon dioxide to dilute any chlorine dioxide gases. After the reaction mixture cooled to about 80° C., 910 ml of 50% sodium hydroxide were carefully and slowly added until a pH-value of 8.5 is reached. The un-reacted quinoline separated and was dissolved in 100 ml of toluol at 40°–50° C. 80 g of quinoline were recovered and used for the next reaction.

The reaction mixture was adjusted with 195 ml of concentrated hydrochloric acid to obtain a pH of 4.5, and 30 g of activated carbon were added. The mixture was stirred for about 15 minutes, was vacuum filtered at 60° C. and extracted three times with 100 ml of 50° C. warm water in each instance. The filtrate was adjusted to a pH of 1 at 50° C. with 640 ml of concentrated hydrochloric acid, and cooled to 0° C. and vacuum filtered. The product was washed sulfate-free with 400 ml of cold water and was dried at 80°–105° C. to obtain 346 g of quinolinic acid (52% of the theory relative to the chinoline used) having an ash content of $<0.1\%$ and an acid number of 667 (in theory 671).

Additional small quantities of quinolinic acid were separated from the mother liquor by precipitation with copper (II)-ions, but because of hard-to-remove residues of copper ions, they were not added to the quinolinic acid precipitated by acidification especially if the quinolinic acid was to be processed further into pharmaceutical preparations.

Various modifications of the process of the invention may be made without departing from the spirit or scope thereof ant it should be understood that the invention is not intended to be limited only as defined in the appended claims.

What we claim is:

1. A process for the preparation of quinolinic acid comprising reacting quinoline in an aqueous acid with hydrogen peroxide in the presence of at least one cation selected from the group consisting of vanadyl V, cobalt III, titanyl IV and osmium VIII cations at 50° to 100° C. and then oxidizing with chlorite or chlorate ions to form quinolinic acid.

2. The method of claim 1 wherein the amount of hydrogen peroxide used is 20 to 90% of that stoichiometrically required for oxidation of quinoline to quinolinic acid.

3. The method of claim 1 wherein the amount of hydrogen peroxide used is 30 to 80% of that stoichiometrically required for oxidation of quinoline to quinolinic acid.

4. The method of claim 1 wherein the sum of hydrogen peroxide and chlorate or chlorite ions used is 120 to 150% of the stoichiometrically required amount.

5. The method of claim 2 wherein the sum of hydrogen peroxide and chlorate or chlorite ions used is 120 to 150% of the stoichiometrically required amount.

6. The method of claim 3 wherein the sum of hydrogen peroxide and chlorate or chlorite ions used is 120 to 150% of the stoichiometrically required amount.

* * * * *